United States Patent [19]

Freedman et al.

[11] Patent Number: 5,134,154
[45] Date of Patent: Jul. 28, 1992

[54] PHENOXY-HETEROCYCLIC COMPOUNDS

[75] Inventors: Jules Freedman, Cincinnati; Mark W. Dudley, Somerville, both of Ohio

[73] Assignee: Merrell Dow Pharmaceuticals Inc., Cincinnati, Ohio

[21] Appl. No.: 665,108

[22] Filed: Mar. 5, 1991

Related U.S. Application Data

[63] Continuation-in-part of Ser. No. 585,547, Sep. 20, 1990, abandoned, which is a continuation-in-part of Ser. No. 424,429, Oct. 20, 1989, abandoned.

[51] Int. Cl.$^5$ .................. C07D 233/22; A61K 31/415
[52] U.S. Cl. ..................................... 514/401; 514/402; 548/348; 548/353
[58] Field of Search ....................... 514/256, 401, 402; 544/333; 548/353, 348

[56] References Cited

U.S. PATENT DOCUMENTS

| | | | |
|---|---|---|---|
| 2,893,993 | 7/1959 | Darnfeld | 260/251 |
| 3,449,355 | 6/1969 | White | 260/309.6 |
| 3,897,431 | 7/1975 | Bailey | 260/251 |

FOREIGN PATENT DOCUMENTS

| | | |
|---|---|---|
| 0011596 | 5/1980 | European Pat. Off. . |
| 614596 | 5/1935 | Fed. Rep. of Germany . |
| 2388496 | 11/1978 | France . |
| 2045240 | 10/1980 | United Kingdom . |

OTHER PUBLICATIONS

Chemical Abstracts, vol. 75, p. 376, #4915r, (1971).
Chemical Abstracts, vol. 70, p. 390, #68371X (1969).
Bailey et al., Amine Functions of Reduced Basicity, Hypoglycemic and Natriuertic a-Alkoxybenzylamidoximes, Amidines and Cycloamidines, Journal of Medicinal Chemistry, vol. 17, No. 7, p. 702 (1974).

*Primary Examiner*—John M. Ford
*Attorney, Agent, or Firm*—William J. Stein

[57] ABSTRACT

The present invention is directed to a new class of phenoxy-heterocyclic compounds and to their use as anti-depressants and as anxiolytics.

10 Claims, No Drawings

PHENOXY-HETEROCYCLIC COMPOUNDS

This is a continuation-in-part of application Ser. No. 585,547 filed on Sept. 20, 1990 which was a continuation-in-part of application Ser. No. 424,429, filed Oct. 20, 1989.

The present invention is directed to a new class of phenoxy-heterocyclic compounds possessing therapeutic properties. Another aspect of the invention is directed to a method for the treatment of depression, anxiety, hypertension, and for the treatment of stroke A further aspect of the invention is directed to pharmaceutical compositions containing these phenoxy-heterocyclic compounds.

In accordance with the present invention, a new class of phenoxy-heterocyclic compounds have been discovered which can be described by the following formula:

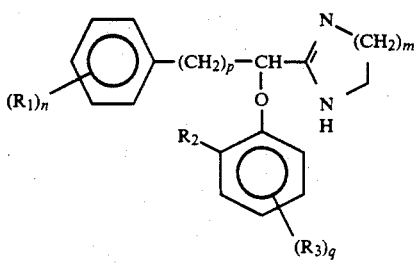

in which $R_1$ is represented by substituent selected from the group consisting of hydrogen, halogen, $C_{1-4}$ alkyl, $C_{1-4}$ alkoxy, OH, $CF_3$, CN, 2,3-methylendioxy, 3,4-methylenedioxy, 2,3-ethylenedioxy, 3,4-ethylenedioxy, $C_{3-5}$ methylene, 2,3-benzo $C_{1-4}$ alkylthio, $C_{1-4}$ alkysulfonyl, $C_{1-4}$ alkylsulfinyl $C_{3-6}$ cycloalkyl, $C_{5-8}$ cycloalkoxy, and $C_{5-8}$ cycloalkylthio; $R_2$ is represented by halogen, $C_{1-4}$ alkyl, $C_{1-4}$ alkoxy, OH, $CF_3$, CN, alkylthio, alkylsulfinyl, $C_{3-6}$ cycloalkyl, $C_{5-8}$ cycloalkoxy or $C_{5-8}$ cycloalkylthio; $R_3$ is represented by hydrogen, halogen, $C_{1-4}$ alkyl, $C_{1-4}$ alkoxy, OH, $CF_3$, CN, 2,3 methylenedioxy, 3,4-methylenedioxy, 4,5-methylenedioxy, 2,3-ethylenedioxy, 3,4-ethylenedioxy, 4,5-ethylenedioxy, $C_{3-5}$ methylene, 2,3-benzo, 3,4-benzo, $C_{1-4}$ alkylthio, $C_{1-4}$ alkylsulfonyl, $C_{1-4}$ alkylsulfinyl, $C_{3-6}$ cycloalkyl, $C_{5-8}$ cycloalkoxy, or $C_{5-8}$ cycloalkylthio; m is represented by the integer 1; n and q are represented by the integers 1 or 2; and p is represented by an integer from 0–4; and the pharmaceutically acceptable addition salts thereof.

The compounds of Formula I exhibit multiple pharmacological properties. They are serotonin $5HT_{1A}$ agonists. The compounds also have an affinity for the α-2 receptor. Due to these pharmacological properties, the compounds are useful in the treatment of depression, anxiety, stroke and hypertension.

As used in this application: a) the term "halogen" refers to a fluorine, chlorine, or bromine atom; b) the terms "lower alkyl group and $C_{1-4}$ alkyl" refer to a branched or straight chained alkyl group containing from 1–4 carbon atoms, such as methyl, ethyl, n-propyl, isopropyl, n-butyl, isobutyl, etc.; c) the terms "lower alkoxy group and $C_{1-4}$ alkoxy" refer to a straight or branched alkoxy group containing from 1–4 carbon atoms, such as methoxy, ethoxy, n-propoxy, isopropoxy, n-butoxy, isobutoxy, etc.; d) the term "methylenedioxy" refers to the following substituent: $-O-CH_2-O-$; e) the term "ethylenedioxy" refers to the following substituent $-O-(CH_2)_2-O-$; f) the term "$C_{3-5}$ methylene" refers to the following substituent $-(CH_2)_n-$, in which n is represented by an integer from 3 to 5; g) the term "alkylthio" refers to the following substituent: $-S-Alk$, in which Alk is represented by a $C_{1-4}$ alkyl; h) the term "alkylsulfonyl" refers to the following substituent: $-SO_2-Alk$, in which Alk is represented by a $C_{1-4}$ alkyl, and; i) the term "alkylsulfinyl" refers to the following substituent: $-SO_2-Alk$, in which Alk is represented by a $C_{1-4}$ alkyl. j) the term "pharmaceutically acceptable addition salt refers to either a basic addition salt or an acid addition salt. k) the term "$C_{3-6}$ cycloalkyl" refers to a cycloalkyl substituent containing from 3-6 carbon atoms such as cyclopropyl, cyclobutyl, cyclopentyl, or cyclohexyl. l) the term "$C_{5-8}$ cycloalkoxy" refers to a cycloalkoxy substituent containing from 5-8 carbon atoms such as cyclopentyloxy, cyclohexyloxy, cycloheptyloxy, or cyclooctyloxy. m) the term "$C_{5-8}$ cycloalkylthio" refers to a cycloalkylthio substituent containing from 5-8 carbon atoms such as cyclopentylthio, cyclohexylthio, cycloheptylthio, or cyclooctylthio.

The expression "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by Formula I or any of its intermediates. Illustrative bases which form suitable salts include alkali metal hydroxides such as sodium or potassium.

All of the compounds of Formula I contain at least one asymmetric center and therefore exist as enantiomers. Any reference in this application to one of the compounds represented by Formula I is meant to encompass either a specific enantiomer or a mixture of enantiomers. The specific enantiomers can be separated and recovered by techniques known in the art such as chromatography on chiral stationary phases or resolution via chiral salt formation and subsequent separation by selective crystallization.

As is apparent to those skilled in the art, the heterocyclic moiety contains a tautomeric center. Thus the double bond contained within this heterocyclic moiety will move freely between the two nitrogen atoms. Any reference in this application to one of the compounds of Formula I should be construed as encompassing either of these tautomers.

The compounds of Formula I contain two phenyl rings. One of these rings may be optionally substituted as indicated by the definition for $R_1$. When $R_1$ is other than a hydrogen atom, there can be up to 5 monovalent substituents occurring on the indicated phenyl ring. These substituents can be the same or different and can be located at any of the ortho, meta, or para positions, If $R_1$ is to be represented by a divalent substituent, such as a methylenedioxy moiety, an ethylenedioxy moity, a benzo moiety or a $C_{3-5}$ methylene moiety, then there can be one of these substituents bonded to the indicated phenyl ring. This phenyl ring may optionally be substituted with one other non-hydrogen monovalent substituent. The divalent substituent can be bonded to either positions 2 and 3 or to positions 3 and 4 of the phenyl ring. Thus the phenyl ring and the divalent substituent will form a bicyclic ring system. These bicyclic ring systems are illustrated below in order to further exemplify the present invention.

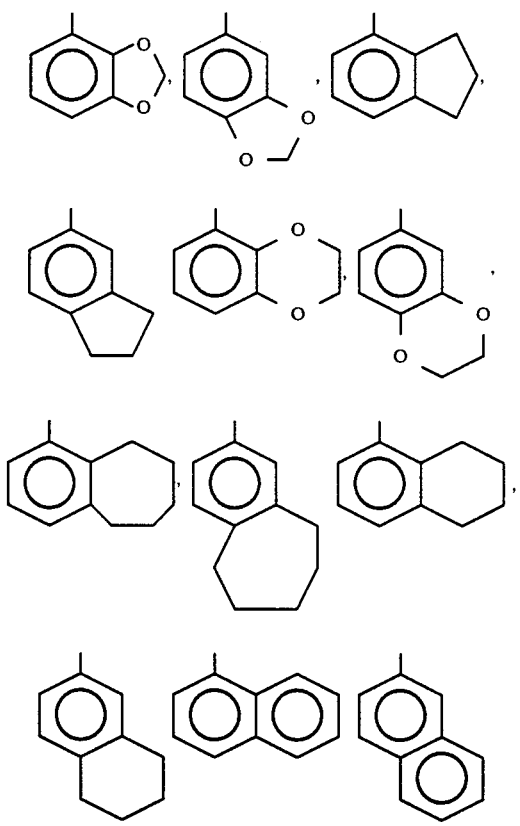

The other phenyl ring must be substituted at the 2-position as is indicated by the definition for $R_2$. This phenyl ring may optionally be further substituted as is indicated by the definition for $R_3$. When $R_3$ is other than a hydrogen atom, there can be up to 4 monovalent substituents bonded to this phenyl ring. These substituents may be located at any of positions 3, 4, 5, or 6. These substituents may be the same or different. $R_3$ may also be represented by a divalent substituent as noted above. This divalent substituent will form ring systems similar to those depicted above except that the divalent substituent may be bonded to positions 3 and 4, positions 4 and 5, or positions 5 and 6. Only one divalent substituent may be bonded to this phenyl ring.

Examination of Formula I shows that the heterocyclic moiety can be represented by either a 5-membered ring or a 6-membered ring. Thus, these compounds can contain either a imidazoline radical or a tetrahydropyrimidine radical.

Illustrative compounds encompassed by Formula I include:

a) 2-[1-(2-ethoxyphenoxy)-2-phenylethyl]imidazoline
b) 2-[u-(2-methoxyphenoxy)benzyl]imidazoline
c) 2-[u-(2-ethoxyphenoxy)benzyl]imidazoline
d) 2-[1-(2-methoxyphenoxy)-2-phenylethyl]imidazoline
e) 2-[1-(2,3-dimethoxyphenoxy)-2-phenylethyl]imidazoline
f) 2-[1-(2-fluoro-4-methoxyphenoxy)-3-phenyl]propyl imidazoline
g) 2-[3-(4-chlorophenyl)-1-(2-methoxyphenoxy)-propyl]g) 1,2,3,4-tetrahydropyrimidine
h) 2-[1-(2-methoxyphenoxy)-3-phenylpropyl]imidazoline
i) 2-[1-(2-ethoxyphenoxy)-3-phenylpropyl]imidazoline The preferred compounds of the instant invention are those in which p is represented by 1. It is also preferred for $R_2$ to be represented by an alkoxy residue and more preferably an ethoxy residue. It is also preferred for $R_3$ to be represented by hydrogen and m to be represented by 1.

The compounds of Formula I can be synthesized using techniques that are known in the art. One method for synthesizing these compounds is disclosed below in Reaction Scheme I.

REACTION SCHEME I
STEP A

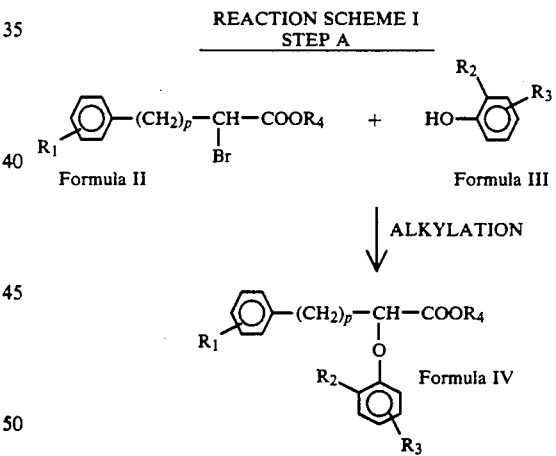

The first step in the reaction sequence is to conduct an alkylation reaction between a bromo ester as described by Formula II and a phenol as described by Formula III. In Formula II, p and $R_1$ are as in Formula I and $R_4$ is represented by a $C_{1-4}$ alkyl. In Formula III, $R_2$ and $R_3$ are as in Formula I.

The appropriate starting materials are a bromo ester in which p and $R_1$ have the same definitions as that desired in the final product and a phenol in which $R_2$ and $R_3$ have the same definitions as that appearing in the final product. The particular $C_{1-4}$ alkyl which is present at the $R_4$ position is immaterial since this substituent will not be retained in the final product The alkylation reaction can be conducted utilizing techniques well known in the art. Approximately equimolar amounts of the bromo ester of Formula II and the phenol of Formula III are contacted in an organic solvent such as acetone or benzene. The reactants are typically contacted in the presence of a base such as $K_2CO_3$. This base is typically present in a molar excess. The reactants are then heated to reflux and the reaction is allowed to proceed for a period of time ranging from about 10 to 96 hours.

The resulting oxy ester intermediate of Formula IV can be recovered from the reaction medium and purified using techniques known in the art. The oxy ester intermediate is typically recovered by concentration as is known in the art. This oxy ester intermediate can then be purified by either distillation or by recrystallization from a solvent such as pentane or hexane using techniques known in the art.

As depicted below in Step B of Reaction Scheme I, the next step in the synthesis is to conduct an amidation reaction between the oxy ester intermediate of Formula IV in which $R_1$, $R_2$, $R_3$ and p are as above, and an alkylene diamine as described by Formula V in which m is represented by 1 or 2. The product of this amidation reaction then cyclizes in-situ thereby producing the desired compound of Formula I. The combination of the amidation and cyclization serves to place the imidazoline or the tetrahydro-pyrimidine moiety on the oxy ester intermediate of Formula IV, thereby producing the desired compound of Formula I.

represented by 2, if a tetrahydro-pyrimidine ring is desired.

This amidation reaction can be conducted using techniques well known in the art. Approximately equimolar amounts of the oxy ester intermediate and the alkylene diamine are contacted in an organic solvent such as toluene. A suitable organo-metallating agent, such as, for example, $Al(CH_3)_3$ is added to the reaction mixture and the reactants are heated to reflux for a period of time ranging from about 3 to 8 hours. Typically from about 1 to about 1.5 equivalents of the organo-metallating agent is utilized. The product of the amidation reaction will cyclize in-situ during this refluxing period, thereby producing the desired compound of formula I.

The resulting compound of Formula I can be recovered and purified by techniques known in the art. For example, the compounds can be recovered from the reaction zone by either concentration or extraction. The compounds of Formula I can then be purified by chromatographic techniques known in the art such as silica gel chromatography Alternatively, they can also be purified by recrystallization from a solvent system such as hexane or cyclohexane.

Methods for producing the phenols of Formula III, the bromo esters of Formula II, and the alkylene diamines of Formula V are known in the art.

Alternatively the oxy intermediates of Formula IV can be prepared as disclosed below in Reaction Scheme II:

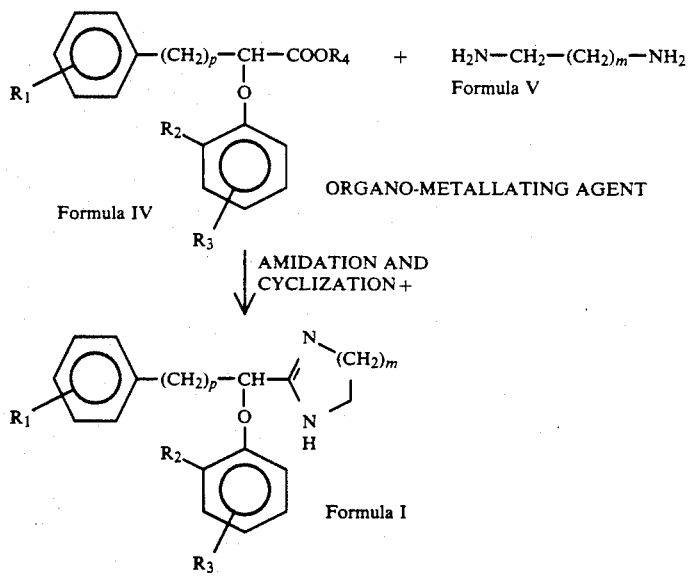

The appropriate alkylene diamine is one in which m is represented by 1, if the desired compound of Formula I is to contain an imidazoline ring and in which m is

REACTION SCHEME II

Step A

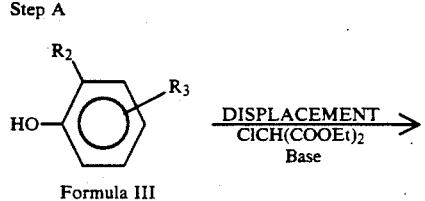

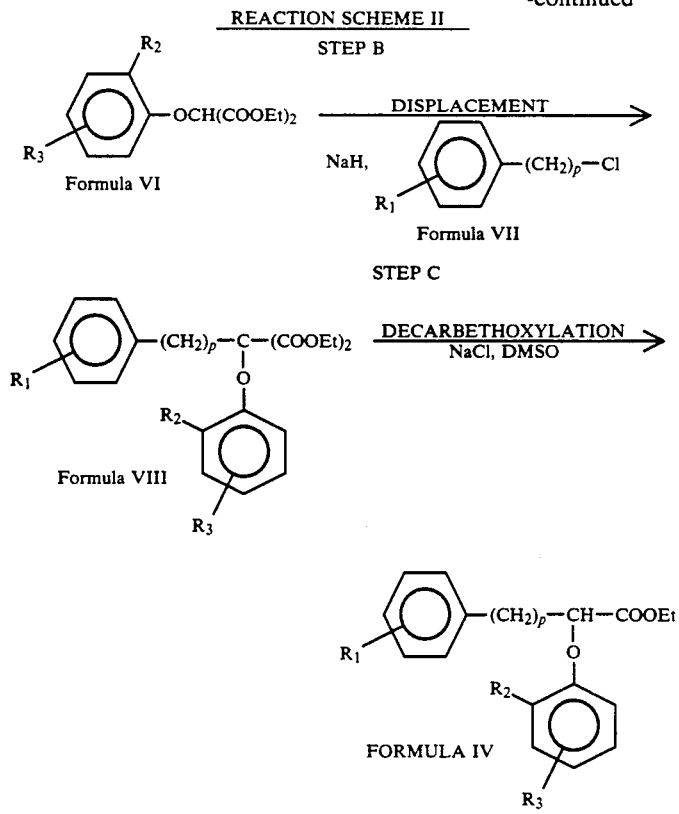

As is depicted in Reaction Scheme II, the initial step is to carry out a displacement reaction between a phenol as previously described by Formula III in which $R_2$ and $R_3$ are as defined above and diethyl chloromalonate. This produces the phenoxy derivative of Formula VI in which $R_2$ and $R_3$ are as in Formula I. In Step B the phenoxy derivative is subjected to a displacement reaction with a chloroalkylphenyl derivative as described by Formula VII in which $R_1$ and p are as in Formula I, which produces the intermediate of Formula VIII. This intermediate is then subjected to a decarbethoxylation reaction which produces the oxy ester of Formula IV in which $R_4$ is an ethyl moiety as depicted. The desired compound of Formula I can then be produced by the amidation and cyclization reaction depicted in Step B of Reaction Scheme I.

The proper starting material to utilize in the displacement reaction of Step A is a phenol derivative in which $R_2$ and $R_3$ are represented by the same substituents as is desired in the final product of Formula I. The displacement reaction of Step A can be carried out using techniqes known in the art. Typically approximately equivalent amounts of the phenol derivative and the diethyl chloromalonate are contacted in the presence of an excess of a base such as potassium carbonate. The reactants are heated to reflux in an organic solvent such as acetone for a period of time ranging from 10 to 48 hours. The desired phenoxy derivatives of Formula VI can be recovered by filtration and purified by distillation as is known in the art.

The displacement reaction of Step B is typically carried out in the following manner. The phenoxy derivative of Formula VI is contacted with 1.1 equivalents of sodium hydride in excess dimethylformamide at a temperature range of from 5 to 10° C. for a period of time from 0.5 to 1 hour. An equivalent amount of the chloroalkylphenyl derivative of Formula VII is then added to the reaction and the reactants are heated to a temperature range of from 55 to 60° C. for a period of time from 2 to 6 hours. The desired intermediates of Formula VIII can be recovered by extraction and purified by distillation as is known in the art.

The decarbethoxylation of Step C is carried out by contacting the intermediate of Formula VIII with approximately 2 equivalents of water, 1 equivalent of NaCl, and an excess of DMSO. The reactants are heated to refluxed under a nitrogen atmosphere for a period of time ranging from 2 to 8 hours. The desired oxy ester of Formula IV can be recovered by extraction and purified by distillation as is known in the art.

The compounds of Formula I are serotonin $5HT_{1A}$ agonists. They also have an affinity for the α-2 receptor. They are useful in the treatment of anxiety, depression, stroke and hypertension.

The affinity of the compounds for the α-2 receptor can be demonstrated by receptor binding assay procedures which are known in the art, such as that described by Perry et al. in the *European Journal of Pharmacology*, Volume 76, pages 461–464 (1981). The affinity of the compounds for the $5HT_{1A}$ receptor can be demonstrated by receptor binding assay procedures such as described by Gozlan et al. in *Nature*, Volume 305, at pages 140–142 (1983). The procedure of Sleight et al., as disclosed in the *European Journal of Pharmacology*, Volume 154, pages 255–261 (1988) can be utilized to show that this affinity results in an agonistic effect upon the receptor.

It has been reported that $5HT_{1A}$ agonists are effective in the treatment of depression. The $5HT_{1A}$ agonist, 8-hydroxy-2-(di-N-propylamino) tetralin (8-OH-DPAT) was shown to be effective in rodent models for depression. *European Journal of Pharmacology*, Vol 144., pages 223-229 (1987) Ceroo et al. and *European Journal of Pharmacoloqy*, Vol 158, pages 53-59 (1988) Ceroo et al. Since the compounds of the instant invention are 5HT$_{1A}$ agonists, they will be useful in the treatment of depression.

In order to exhibit an anti-depressant effect, it is necessary that the compounds be administered to the patient in an effective amount. The dosage range at which these compounds exhibit this anti-depressant effect can vary widely depending upon the severity of the patient's depression, the particular compound being administered, the route of administration, the co-administration of other therapeutic agents, and the presence of other underlying disease states. Typically, the compounds will be administered at a dosage range of from 0.1 mg/kg/day to about 100 mg/kg/day. Repetitive daily administration may be desirable and will vary with the conditions described above. However, the compounds are typically administered from 1 to 4 times daily.

As used in this application, the term "depression" should be construed as encompassing those conditions which the medical profession have referred to as major depression, endogenous depression, psychotic depression, involutional depression, involutional melancholia, etc. These conditions are used to describe a condition in which patients typically experience intense sadness and despair, mental slowing, loss of concentration, pessimistic worry, despair, and agitation. The patients often experience physical complaints such as insomnia, anorexia, decreased energy, decreased libido, etc.

The compounds of Formula I will elevate the patient's mood if they are suffering from depression and either relieve or alleviate the physical complaints which the patient is experiencing.

As noted above, the compounds of Formula I are serotonin 5HT$_{1A}$ agonists. Compounds producing this effect at the 5HT$_{1A}$ receptor have also been found to exhibit anxiolytic properties. *European Journal of Pharmocology*, Vol. 88, pages 137-138 (1983) Gloser et al. and Drugs of the Future Vol. 13 pages 429-439 (1988) Glaseat. A 5HT$_{1A}$ agonist known as buspirone is currently being marketed as an anxioltyic agent. Since the compounds of the instant invention are 5HT$_{1A}$ agonists, they will be useful in the treatment of anxiety. The anxiolytic properties of these compounds can also be demonstrated by their ability to block distress vocalizations in rat pups. This test is based upon the phenomenon that when a rat pup is removed from its litter, it will emit an ultrasonic vocalization. It was discovered that anxiolytic agents block these vocalizations. The testing methods have been described by Gardner, C.R., Distress vocalization in rat pups: a simple screening method for anxiolytic drugs. *J. Pharmacol. Methods*, 14: 181-187 (1985) and Insel et al., Rat pup ultrasonic isolation calls: Possible mediation by the benzodiapine receptor complex, *Pharmacol. Biochem. Behav.*, 24: 1263-1267 (1986).

As used in this application, the term "anxiety" refers to:

The unpleasant emotional state consisting of psychophysiological responses to anticipation of unreal or imagined danger, ostensibly resulting from unrecognized intrapsychic conflict. Physiological concomitants include increased heart rate, altered respiration rate, sweating, trembling, weakness, and fatigue; psychological concomitants include feelings of impending danger, powerlessness, apprehension, and tension.

In order to exhibit this anxiolytic effect, it is necessary that the compounds be administered to the patient in an effective amount. The dosage range at which these compounds exhibit this anxiolytic effect can vary widely depending upon the severity of the patient's anxiety, the particular compound being administered, the route of administration, the co-administration of other therapeutic agents, and the presence of other underlying disease states. Typically, the compounds will be administered at a dosage range of from about 0.1 mg/kg/day to about 100 mg/kg/day. Repetitive daily administration may be desirable and will vary with the conditions described above. However, the compounds are typically administered from 1 to 4 times daily.

Serotonin 5HT$_{1A}$ agonists have also been shown to produce a hypotensive effect. For example, the 5HT$_{1A}$ agonists, 8-OH-DPAT and Flesinoxan, have been shown to lower blood pressure Dreteler et al., *European Journal Pharmacology*, 180, pages 339-349 (199c). Since the compounds of Formula I are 5HT$_{1A}$ agonists, they will be useful in the treatment of hypertension. The anti-hypertensive properties of the compounds can be demonstrated by animal models known in the art such as the spontaneously hypertensive rat. This protocol has been described by Dage et al., *Journal of Cardiovascular Pharmacology* 3: 299-315 (1981).

In order to exhibit an antihypertensive effect, it is necessary that the compounds be administered to the patient in an effective amount. The dosage range at which these compounds exhibit this effect can vary widely depending upon the severity of the patient's condition, the particular compound being administered, the route of administration, the co-administration of other therapeutic agents, and the presence of other underlying disease states. Typically, the compounds will be administered at a dosage range of from 0.01 mg/kg/day to about 100 mg/kg/day. Repetitive daily administration may be desirable and will vary with the conditions described above. However, the compounds are typically administered from 1 to 4 times daily.

Serotonin 5HT$_{1A}$ agonists have also been shown to be useful in the treatment of stroke. It has been discovered that these compounds exhibit a neuroprotective effect and will either relieve or inhibit the CNS damage that typically accompanys a stroke. This neuroprotective effect is believed to be due to serotonin's inhibitory effect upon excitatory neurotransmission. For example, Bielenberg et al showed that the 5HT$_{1A}$ agonists 8-OH-DPAT, buispirone, gepirone, ipsapirone, and Bay R 1531 inhibited or decreased neuronal destruction in rodent models of stroke. *Stroke Supplement IV*, Volume 21, No. 12 (Dec., 1990). Since the compounds of Formula I are serotonin 5HT$_{1A}$ agonists, they will be useful in the treatment of stroke.

In order to exhibit this neuroprotective effect, it is necessary that the compounds be administered to the patient in an effective amount. The dosage range at which these compounds exhibit this effect can vary widely depending upon the severity of the patient's condition, the particular compound being administered, the route of administration, the co-administration of other therapeutic agents, and the presence of other underlying disease states. Typically, the compounds will be administered at a dosage range of from 0.01 mg/kg/day to about 100 mg/kg/day. Repetitive daily administration may be desirable and will vary with the conditions described above. However, the compounds are typically administered from 1 to 4 times daily or as a continuous intravenous infusion.

Stroke is a condition in which injury to the brain results due to either ischemic or hemmoragic lesions. It is also commonly referred to as a cerebrovascular accident. The compounds of Formula I can be used to treat any of these conditions. As used herein, the phrase "treating stroke" refers to the ability of the compounds to either inhibit or decrease the CNS damage that typically accompanys a stroke.

As is readily apparent to those skilled in the art, the compounds of Formula I will not correct any CNS damage that has already occurred as the result of the cardiovascular accident. The compounds should be administered at the initiation of the cardiovascular accident or soon thereafter, prior to the occurrence of extensive CNS damage.

The compounds of the present invention may be administered by a variety of routes. They are effective if administered orally. The compounds may also be administered parenterally (i.e. subcutaneously, intravenously, intramuscularly, or intraperitoneally).

As used in this application: a) the term "patient" refers to warm blooded animals such as, for example, guinea pigs, mice, rats, cats, rabbits, dogs, monkeys, chimpanzees, and humans; b) the term "treat" refers to the ability of the compounds to either relieve, alleviate, or slow the progression of the patient's disease.

Pharmaceutical compositions can be manufactured utilizing techniques known in the art. Typically an antidepressant or anxiolytic amount of the compound will be admixed with a pharmaceutically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compounds of Formula I can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art.

The compounds of Formula I may also be admixed with any inert carrier and utilized in laboratory assays in order to determine the concentration of the compounds within the serum, urine, etc., of the patient as is known in the art.

EXAMPLE I

The purpose of this example is to demonstrate the alkylation reaction between a bromo ester as described by Formula II and an alcohol as described by Formula III which is described in Step A of Reaction Scheme I.

Ethyl α-(2-Methoxyphenoxy)-phenylacetate

A mixture of 130 g (1.05 m) guaiacol, 243 g (1 M) ethyl α-bromophenylacetate, 150 g of potassium carbonate and 1.5 L of acetone was refluxed for 96 hours, cooled and filtered. The solvent was removed at reduced pressure and the residue dissolved in toluene. After washing with dilute sodium hydroxide, then water, the solvent was removed and the residue distilled. The fraction boiling at 158–163°/0.4 mm was collected, weight 263 g.
Anal., Calcd. for $C_{17}H_{18}O_4$: C=71.21; H=6.34,
Fd.: C=71.26; H=6.49.
Similarly prepared were:
Ethyl α-phenoxyphenylacetate (literature compound)
Ethyl 2-(2-ethoxyphenoxy)phenylacetate
Boiling Point 130-138° C./0.05 mm
Anal., Calcd. for $C_{18}H_{20}O_4$: C=71.98; H=6.71,
Fd.: C=71.71; H=6.73.
Ethyl 2-(2-methoxyphenoxy)-3-phenylpropionate
Boiling Point 130–40° C./0.3 mm
Anal., Calcd. for $C_{18}H_{20}O_4$: C=71.98; H=6.71,
Fd.: C=72.32; H=6.64.
Ethyl 2-(2,3-dimethoxyphenoxy)-3-phenylpropionate
Boiling Point 150–58° C./0.3 mm
Anal., Calcd. for $C_{19}H_{22}O_5$: C=69.07; H=6.71,
Fd.: C=69.16; H=6.69.
Ethyl 2-(2-ethoxyphenoxy)-3-phenylpropionate
Boiling Point 130–35° C./0.25 mm
Anal., Calcd. for $C_{19}H_{22}O_4$: C=72.59; H=7.05,
Fd.: C=72.39; H=6.98.
Ethyl 2-(2-methoxyphenoxy)-4-phenylbutyrate
Boiling Point 143–48° C./0.1 mm
Anal Calcd for $C_{19}H_{22}O_4$: 72.59; H=7.05,
Fd.: C=72.50; H=7.05.
Ethyl 2-(2-ethoxyphenoxy)-4-phenylbutyrate
Boiling Point 175–82° C./0.5 mm
Anal Calcd. for $C_{20}H_{24}O_2$: C=73.14; H=7.37,
Fd.: C=72.75; H=7.25.
Ethyl 2-(2,6-Dimethoxyphenoxy)phenylacetate
Boiling Point 165–75° C./0.3 mm
Anal. Calcd. for $C_{18}H_{20}O_5$: C=68.34; H=6.37,
Fd.: C=68.36; H=6.42.
Using the methods taught above but substituting the appropriate starting material, the following compounds can be prepared.
Ethyl 2-(2-methoxyphenoxy)-4-phenylbutyrate
Ethyl 2-(2-ethoxyphenoxy)-5-phenylvalerate
Ethyl 2-(2-methoxyphenoxy)-2-(3,4-dichlorophenyl)acetate
Methyl 2-(2,5-dimethoxyphenoxy)-4-phenylbutyrate
Ethyl 2-(2-isopropylthiophenoxy)-3-phenylpropionate
Ethyl 2-(4-chlorophenoxy)phenylacetal.

EXAMPLE II

The purpose of this example is to demonstrate a displacement reaction depicted in Step A of Reaction Scheme II.

A) Diethyl 2-(isopropoxy)phenoxymalonate
A mixture of 25 g (0.16 M) diethyl chloromalonate, 25 g potassium carbonate and 320 ml of acetone was refluxed for 24 hours, cooled and filtered. The solvent was removed from the filtrate and the residue taken up in ether, washed with water and dried over sodium sulfate. Removal of the solvent and distillation gave 36.3 g boiling at 145-148° /0.2 mm. Anal. Calcd. for $C_{16}H_{22}O_6$: C=71.92; H=7.15.

Fd: C=61.44: H=7.06.
Similarly prepared were:
Diethyl 2-ethoxyphenoxymalonate
Boiling point 155-162° /0.3 mm
Anal. Calcd. for $C_{15}H_{20}O_6$: C=60.80; H=6.80,
Fd: C=60.73; H=6.73.
Diethyl 2-methylthiophenoxymalonate
Boiling point 177-182° C./0.3 mm
Anal. Calcd for $C_{21}H_{24}O_5S$: C=64.92; H=6.23,
Fd: C=64.75; H=6.24.

This example demonstrates the displacement reaction of Step B in Reaction Scheme II.

B) DiethVl α-benzVl-α-[2-(isopropoxV)phenoxy]-malonate

To an ice-cooled suspension of sodium hydride (from 2.2 g of a 60% mixture with oil) is added 100 ml of dimethylformamide, a solution of 16.1 g (0.05 M) of diethyl 2-(isopropoxy)phenoxymalonate in 25 ml of dimethylformamide was added dropwise. After stirring 20 minutes at room temperature a solution of 7.0 g (0.055 M) of benzyl chloride in 10 ml of dimethylformamide was added all at once and the mixture was heated in an oil bath at 55-60° for 2 hours. The mixture was cooled in ice and excess sodium hydride was decomposed with acetic acid. The reaction mixture was diluted with water and extracted with ethyl acetate. The ethyl acetate was removed from the extracts and the residue was shaken with a mixture of acetonitrile and pentane. Concentration of the acetonitrile layer and distillation gave 17.5 g, b.p. 175-185°/0.2 mm.

Anal. Calcd. for $C_{23}H_{28}O_6$: C=68.98; H=7.05,
Fd: C=68.83; H=7.05.
Similarly prepared were:
Diethyl α-(4-fluorobenzyl)-o-(2-ethoxyphenoxy)malonate
Boiling point 180-183° /0.3 mm
Anal. Calcd. for $C_{22}H_{25}OF_6$: C=65.33; H=6.23,
Fd: C=65.23; H=6.45.
Diethyl α-(4-t-butyl-2,6-dimethylbenzyl)-α-(2-ethoxyphenoxy)malonate Boiling point 178-187° /0.2 mm
Anal. Calcd. for $C_{27}H_{38}O_6$: C=70.71; H=8.35,
Fd: C=70.57; H=8.62.

This example demonstrates the decarbethoxylation reaction of Step C in Reaction Scheme II. C) Ethyl 2-(2-isopropoxyphenoxV)-3-phenyl propionate A mixture of 17.2 g (0.043 M) of diethyl α-benzyl-2isopropoxyphenoxymalonate, 2.5 g (0.04 M) sodium chloride, 1.55 g (0.085 M) water and 120 ml of dimethylsulfoxide was refluxed under nitrogen for 6 hours, cooled and diluted with water. The mixture was extracted with two 500 ml portions of 4:1 pentane-ether and the extracts dried over magnesium sulfate. Removal of the solvent and distillation gave 10.6 g, b.p. 138-143°/0.3 mm.

Anal. Calcd. for $C_{20}H_{24}O_4$: C=73.14; H=7.37,
Fd: C=72.54; H=7.42.
Similarly prepared were:
Ethyl 2-(ethoxyphenoxy)-3-(4-fluorophenyl)propionate
Boiling Point 137-143° /0.3 mm
Anal. Calcd. for $C_{19}H_{21}OF_4$: C=67.48; H=6.61,
Fd: C=68.05: H=6.39.

Ethyl 2-(ethoxyphenoxy)-3-(4-methoxyphenyl)propionate
Boiling Point 175-178° /0.4 mm
Anal. Calcd for $C_{20}H_{24}O_5$: C=69.78; H=7.02,
Fd: C=69.67; H=7.11.

EXAMPLE III

The purpose of this example is to demonstrate the amidation and cyclization reaction which is described in Step B of Reaction Scheme I.

2-[1-(2-ethoxyphenoxy)-2-phenylethyl]imidazoline

A mixture of 6.28 g (0.02 m) of ethyl 2-(2-ethoxyphenoxy)-3-phenylpropionate, 1.93 g (0.033 m) ethylenediamine and 150 ml of dry toluene was stirred at room temperature and 17 ml of a 2 m solution of trimethylaluminum in toluene was added dropwise. After stirring 10 minutes, the mixture was heated at reflux for 3 hours, then cooled in an ice bath. Water (10 ml) was added followed by 20 ml methanol and the mixture heated on a steam bath for 0.5 hours. Solids were filtered and the solvent evaporated. The solid residue was recrystallized from cyclohexane to give 3.53 g, melting point 95-97° C. Anal., Calcd. for $C_{19}H_{22}N_2O_2$: C=73.52; H=7.14; N=9.0,
Fd C=73.65; H=7.21; N=8.93.
Similarly prepared were:
2-[α-(2-methoxyphenoxy)]benzylimidazoline
Melting Point 123-25° C.
Anal. Calcd. for $C_{17}H_{18}N_2O_2$: C=72.32; H=6.43; N=9.92,
Fd.: C=72.08; H=6.45; N=9.79.
2-[α-(2-Ethoxyphenoxy)]benzylimidazoline
Melting Point 116-18° C.
Anal. Calcd. for $C_{18}H_{20}N_2O_2$: C=72.94; H=6.80; N=9.45,
Fd.: C=72.86; H=6.84; N=9.44.
2-[1-(2-methoxyphenoxy)-2-phenylethyl]imidazoline
Melting Point 97-100° C.
Anal. Calcd. for $C_{18}H_{20}N_2O_2$: C=72.94; H=6.80; N=9.45,
Fd.: C=72.48; H=6.80; N=9.58.
2-[1-(2-ethoxyphenoxy)-2-phenylethyl]imidazoline
Melting Point 95-97° C.
Anal. Calcd. for $C_{19}H_{22}N_2O_2$: C=73.52; H=7.14; N=9.03,
Fd C=73.65; H=7.21; N=8.93.
2-[1-(2,3-dimethoxyphenoxy)-2-phenylethyl]imidazoline
Melting Point 86-87° C.
Anal. Calcd. for $C_{19}H_{22}N_2O_3$: C=69.92: H=6.79; N=8.58,
Fd.: C=69.72; H=6.84; N=8.51
1-(2-methoxyphenoxy)-3-phenylpropyl]imidazoline
Melting point 117-118° C.
Anal. Calcd. for $C_{19}H_{22}N_2O_2$: C=73.52; H=7.14; N=9.03,
Fd.: C=73.53; H=7.23, N=8.96.
2[1-(2-ethoxyphenoxy)-3-phenylpropyl]imidazoline
Melting Point 74-77° C.
Anal. Calcd. for $C_{20}H_{24}N_2O_2$: C=74.04; H=7.46; N=8.64,
Fd.: C=73.84; H=7.52; N=8.49.
2-[1-(2-Ethoxyphenoxy)-2-phenylethyl]-1,2,3,4tetrahydropyrimidine
Melting point 98-100° C.
Anal. Calcd. for $C_{20}H_{24}N_2O_2$: C=74.04; H=7.46; N=8.64, Fd: C=73.90; H=7.52; N=8.44.

2-[1-(2-Ethoxyphenoxy)-(4-fluorophenyl)ethyl]imidazoline

Melting point 103–105° C.

Anal. Calcd. for $C_{19}H_{21}FN_2O_2$ C=69.49; H=6.45; N=8.53,

Fd: C=69.23; H=6.48; N=8.70.

2-[1-(2-Ethoxyphenoxy)-(4-methoxyphenyl)ethyl]imidazoline

Melting point 89–91° C.

Anal. Calcd. for $C_{20}H_{24}FN_2O_3$: C=70.56; H=7.11; N=8.2,

Fd: C=70.61; H=7.24; N=8.25.

2-[1-(2-Ethoxyphenoxy)-(4-t-butyl-2,6-dimethylphenyl)ethyl]imidazoline oxalate

Melting point 205–207° C.

Anal. Calcd. for $C_{25}H_{34}FN_2O_2 \cdot C_2H_2O_4$: C=66.92; H=7.49; N=5.781, Fd: C=66.95; H=7.71; N=5.67.

2-[1-(2-Isopropoxyphenoxy)-2-phenylethyl]imidazoline

Melting point 81–83° C.

Anal. Calcd. for $C_{20}H_{24}N_2O_2$: C=74.27; H=7.17; N=8.66,

Fd: C=73.87; H=7.50; N=8.38.

2-[α-(2-Cyclopentyloxy)-2-phenylethyl]imidazoline

Melting point 110–112° C.

Anal. Calcd. for $C_{22}H_{26}N_2O_2$: C=75.40; H=7.48; N=7.99,

Fd: C=75.10; H=7.46; N=7.7.

2-[1-(2-Ethoxy-5-methoxphenoxy)-2-phenylethyl]imidazoline oxalate

Melting point 132–134° C.

Anal. Calcd. for $C_{20}H_{24}N_2O_3 \cdot C_2H_2O_4$: C=61,38; H=6.09; N=6.5,

Fd: C=61.46; N=6.48.

2-[1-(2,6-Dimethylphenoxy)-2-phenylethyl]imidazoline

Melting Point 119–122° C.

Anal. Calcd. for $C_{19}H_{22}N_2O$: C=77.51; H=7.53; N=9.52,

Fd: 77.40; H=7.68; N=9.29.

2-[α-(2,3-Dimethoxyphenoxy)benzyl]imidazoline

Melting point 86–87° C.

Anal. CalCd. for $C_{19}H_{22}N_2O_3$: C=69.92; H=6.79; N=8.58,

Fd: C=69.72

H=6.84; N=8.51.

Using the methods taught above, but substituting the appropriate starting material, the following compounds may be prepared.

2-[1-(2-methoxyphenoxy)-2-phenylethyl]imidazoline

2-[1-(2-methylphenoxy)-2-(4-chlorophenyl)ethylimidazoline

2-[1-(2-fluoro-4-methoxyphenoxy)-3-phenylpropyl]imidazoline

2-[2-(4-methoxyphenyl)-1-(2-methoxyphenoxy)ethyl]imidazoline

2-[3-(4-chlorophenyl)-1-(2-methoxyphenoxy)propyl]-1,2,3,4tetrahydropyrimidine

2-[1-(2(2-methylthiophenoxy)-2-phenylethyl]imidazoline

Melting point 112–114° C.

Anal. Calcd. for C=69.19; H=6.45; N-8.97,

Fd: C=69.20; H=6.58; N=8.96.

2-[1-(Isopropylthiophenoxy)-2-phenyl]-ethyl imidazoline

Melting point 90–92° C.

Anal. Calcd. for $C_{20}H_{24}N_2OS$: C=70.55; H=7.11; N=8.23,

Fd: C=70.41; H=7.38; N=8.13.

What is claimed is:

1. A compound of the formula:

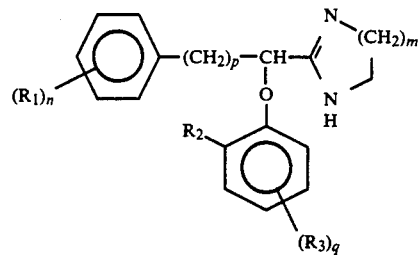

in which $R_1$ is represented by hydrogen, halogen, $C_{1-4}$ alkyl, $C_{1-4}$ alkoxy, OH, $CF_3$, CN, 2,3-methylenedioxy, 3,4-methylenedioxy, 2,3-ethylenedioxy, 3,4-ethylenedioxy, $C_{3-5}$ methylene, 2,3-benzo, 3,4-benzo, $C_{1-4}$ alkylthio, $C_{1-4}$ alkylsulfonyl, $C_{1-4}$ alkylsulfinyl, $C_{3-6}$ cycloalkyl, $C_{5-8}$ cycloalkoxy or $C_{5-8}$ cycloalkylthio; $R_2$ is represented by halogen, $C_{1-4}$ alkyl, $C_{1-4}$ alkoxy, OH, $CF_3$, CN, alkylthio, alkylsulfinyl, $C_{3-6}$ cycloalkyl, $C_{5-8}$ cycloalkoxy or $C_{5-8}$ cycloalkylthio; $R_3$ is represented by hydrogen, halogen, $C_{1-4}$ alkyl, $C_{1-4}$ alkoxy, OH, $CF_3$, CN, 2,3-methylenedioxy, 3,4-methylenedioxy, 4,5-methylenedioxy, 2,3-ethylenedioxy, 3,4-ethylenedioxy, 4,5-ethylenedioxy, $C_{3-5}$ methylene, 2,3-benzo, $C_{1-4}$ alkylthio, $C_{1-4}$ alkylsulfonyl, $C_{1-4}$ alkylsulfinyl, $C_{3-6}$ cycloalkyl, $C_{5-8}$ cycloalkoxy or $C_{5-8}$ cycloalkylthio; m is represented by the integer 1; n and q are represented by the integers 1 or 2; p is represented by an integer from 0–4; and the pharmaceutically acceptable addition salts thereof.

2. A compound according to claim 1 wherein p is represented by 1.

3. A compound according to claim 1 wherein $R_2$ is alkoxy.

4. A compound according to claim 1 wherein $R_2$ is ethoxy.

5. A compound according to claim 1 wherein $R_3$ is hydrogen.

6. A method for the treatment of depression comprising administering an anti-depressant amount of a compound according to claim 1.

7. A method for the treatment of anxiety comprising administering an anxiolytic amount of a compound according to claim 1.

8. A method for the treatment of hypertension comprising administering a hypertensive effective amount of a compound according to claim 1 to a patient in need thereof.

9. A pharmaceutical composition comprising a compound according to claim 1 in admixture with an inert carrier.

10. A method for the treatment of stroke comprising administrating a neuroprotective amount of a compound according to claim 1 to a patient in need thereof.

* * * * *

UNITED STATES PATENT AND TRADEMARK OFFICE
CERTIFICATE OF CORRECTION

PATENT NO. : 5,134,154

DATED : July 28, 1992

INVENTOR(S) : Jules Freedman & Mark W. Dudley

It is certified that error appears in the above-identified patent and that said Letters Patent is hereby corrected as shown below:

Column 1, line 11, "stroke A" should read -- stroke. A --. Column 1, line 37, "2,3-benzo $C_{1-4}$ alkylthio," should read -- 2,3-benzo, 3,4 benzo, $C_{1-4}$ alkylthio, -- Column 2, line 10, "-$SO_2$-Alk," should read -- -SO-Alk, --. Column 3, line 9, "positions," should read -- positions. --. Column 4, line 11, "2-[u-" should read -- 2-[α- --. Column 4, line 12, "2-[u-" should read -- 2-[α- --. Column 4, line 19, "propyl]g) 1," should read -- propyl]-1, --. Column 9, line 5, "Pharmacoloqy" should read -- Pharmacology --. Column 10, line 20, "pressure" hould read -- pressure, --. Column 10, line 47, "accomnpanys" should read -- accompanies --. Column 11, line 11, "accompanys" should read -- accompanies --. Column 13, line 19, "B) DiethVl α-benz Vl... (isopropoxV)" should read -- B) Diethyl α-benzyl... (isopropoxy) --. Column 13, line 21, "oil}is" should read -- oil) is --. Column 13, line 43, "$OF_6$...6.23," should read -- $FO_6$...6.23 --. Column 13, line 51, "-isopropoxyphenoxV)" should read -- -isopropoxyphenoxy) --. Column 13, line 53, "-2isopro..." should read -- -2-isopro... --. Column 13, line 66, "$OF_4$" should read -- $FO_4$ --. Column 14, line 25, "N=9.0," should read -- N=9.03, --. Column 14, line 54, "1-(2-methoxy..." should read -- 2-[1-(2-methoxy... --. Column 14, line 56, "H22" should read -- $H_{22}$ --. Column 14, line 64, "4tet" should read -- 4-tet --. Column 15, line 18, "N=5.781," should read -- N=5.78, --. Column 15, line 31, "N=7.7." should read -- N=7.73. --. Column 15, line 35, "N=6.5," should read -- N=6.51, --. Column 15, line 61, "4tetra..." should read -- 4 tetra... -- Column 16, line 34, "2,3-benzo, $C_{1-4}$..." should read -- "2,3-benzo, 3,4-benzo, $C_{1-4}$... --.

Signed and Sealed this

Sixteenth Day of November, 1993

Attest:

BRUCE LEHMAN

Attesting Officer

Commissioner of Patents and Trademarks